United States Patent [19]

Pawloski

[11] 4,387,058

[45] Jun. 7, 1983

[54] CARBAMIC ACID DERIVATIVES

[75] Inventor: Chester E. Pawloski, Bay City, Mich.

[73] Assignee: The Dow Chemical Company, Midland, Mich.

[21] Appl. No.: 307,962

[22] Filed: Oct. 2, 1981

[51] Int. Cl.$^3$ .................. C07C 121/50; C07C 121/62; C07C 125/067

[52] U.S. Cl. .................................. 260/465 D; 560/20; 560/21; 560/29; 560/73; 560/100; 560/108; 560/109; 560/110; 560/134; 560/135; 560/136; 560/137; 71/98; 71/105; 71/106; 71/111

[58] Field of Search ................. 560/29, 137, 134, 135, 560/136, 73, 20, 21, 108, 109, 100, 110; 260/465 D

[56] References Cited

U.S. PATENT DOCUMENTS 3,971,822  7/1976  Chibata et al. .......... 560/29
4,002,666  1/1977  Shirai et al. ............. 560/29
4,090,862  5/1978  Thomas et al. .......... 560/29

*Primary Examiner*—Delbert R. Phillips
*Assistant Examiner*—Frederick W. Pepper
*Attorney, Agent, or Firm*—John M. Sanders

[57] ABSTRACT

Novel phenyl and naphthyl esters of 2-(1-oxo-alkoxy)ethyl carbamic acids are prepared. The compounds are useful as pharmacological and agricultural agents.

6 Claims, No Drawings

CARBAMIC ACID DERIVATIVES

SUMMARY OF THE INVENTION

The present invention relates to carbamic acid derivatives corresponding to the formula

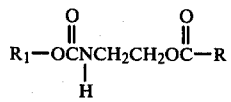

wherein
  R represents 1-8C alkyl, phenyl or naphthyl, said phenyl and naphthyl groups being optionally substituted with one or more halo, nitro, cyano, 1-8C alkoxy, 1-8C alkyl or 1-8C alkylthio groups; and
  $R_1$ represents phenyl or naphthyl optionally substituted with one or more halo, nitro, 1-8C alkoxy, 1-8C alkyl, cyano, or 1-8C alkylthio groups.

The compounds of the present invention are crystalline solids at ambient room temperature which have low solubility in water and which are only slightly soluble in common organic solvents such as dimethylformamide, dimethylsulfoxide and acetonitrile.

These compounds are prepared by reacting an appropriate phenol or naphthol compound with an appropriate isocyanatoethyl compound. The reaction can be characterized as follows:

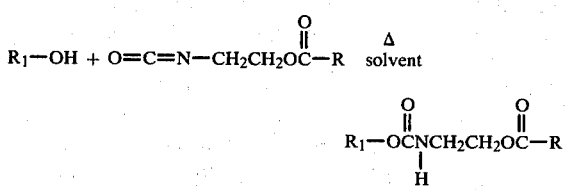

wherein $R_1$ and R are as defined above.

In carrying out the reaction the above-identified reactants are advantageously mixed in equimolar proportions in an inert solvent such as toluene, acetonitrile or methyl ethyl ketone. The order of mixing the reactants is not critical. To this mixture it is advantageous to add a tin catalyst such as dibutyl tin laurate. The reactants are maintained under agitation during the reaction period. The reaction is maintained at temperatures between about 25° C. and about 100° C. and preferably at the reflux temperature of the solvent. The reaction is usually complete in from about 2 to about 24 hours. Upon completion of the reaction, the reaction mixture is allowed to cool and the solvent is removed by distillation leaving the desired product which may then be purified employing conventional purification procedures.

DESCRIPTION OF SOME PREFERRED EMBODIMENTS

The term "herbicide" is used herein to mean an active ingredient which controls or modifies the growth of plants. By a "growth-controlling" or "herbicidally-effective" amount is meant an amount of active ingredient which causes a modifying effect and includes deviations from natural development, such as, for example, killing, retardation, defoliation, desiccation, regulation, stunting, tillering, stimulation, dwarfing and the like. The terms "plants" is meant to include germinant seeds, emerging seedlings and established vegetation, including the roots and above-ground portions thereof. The term "antimicrobial" as employed herein includes both antibacterial and antifungal action of the compounds. The term "1-8C" when used herein to describe alkoxy, alkyl and alkylthio group means such groups containing from 1 to 8 carbon atoms.

The following examples illustrate the present invention and the manner by which it can be practiced but, as such, should not be construed as limitations upon the overall scope of the same.

EXAMPLE 1

2,4,5-Trichlorophenyl ester of (2-(acetyloxy)ethyl)carbamic acid

A mixture of 6.5 grams (g) (0.05 mole) of 2-isocyanatoethyl acetate, 9.9 g (0.05 mole) of 2,4,5-trichlorophenol, 200 milliliters (ml) of methyl ethyl ketone and a drop of dibutyl tin dilaurate was stirred at reflux for 7 hours and thereafter allowed to cool to room temperature. The solvent was removed by distillation under reduced pressure and the resulting oil was stirred into 400 ml of n-hexane. The resulting solids were filtered off, rinsed with n-hexane and dried to give 14.4 g of the above captioned compound having a melting point of 91°-93° C.

EXAMPLE 2

2-(1-Methylpropyl)-4,6-dinitrophenyl ester of (2-1-oxopropoxy)ethyl)carbamic acid A mixture of 12 g (0.05 mole) of 2,4-dinitro-6-sec.-butylphenol, 7.2 g (0.05 mole) of 2-isocyanatoethyl propionate, 200 ml methyl ethyl ketone and a few drops of dibutyl tin dilaurate were refluxed, with stirring, for 8 hours. After the mixture was allowed to cool to room temperature 0.005 mole of potassium carbonate was added to precipitate out any impurities and the mixture was again refluxed with stirring for 8 more hours after which the mixture was then allowed to cool. The solids were then filtered off and liquid phase was distilled under reduced pressure to remove the solvent. The resulting solids were slurried in n-hexane, filtered off and dried giving a 95% yield of the above captioned compound having a melting point of 242° C. with decomposition.

EXAMPLE 3

Employing substantially the same procedure of Example 2 the following compounds were prepared by reacting the appropriate starting compounds: pentachlorophenyl ester of (2-(1-oxopropoxy)ethyl)carbamic acid, m.p. 150° C./decomposition; 2,4-dichloronaphthyl ester of (2-(1-oxopropoxy)ethyl carbamic acid, m.p. 97°-99° C.; and 2-cyano-6-nitrophenyl ester of (2-(1-oxopropoxy)ethyl)carbamic acid; m.p. 61°-71° C.

The structure of each compound prepared in the above examples was confirmed by nuclear magnetic resonance (NMR) spectra.

In accordance with the present invention, it has been discovered that such compounds can be employed as antimicrobials and herbicides. Some compounds have both types of activity. This is not to suggest that all of the compounds are equally effective against the same plants or organisms or at the same concentrations.

For plant growth control and antimicrobial usage, the compounds can be employed in an unmodified form or dispersed on a finely divided solid and employed as dusts. Such mixtures can also be dispersed in water with or without the aid of a surface-active agent and the resulting aqueous suspensions employed as sprays. In other procedures, the products can be employed as active constituents in solvent solution, oil-in-water or water-in-oil emulsions or aqueous dispersions. The augmented compositions are adapted to be formulated as concentrates and subsequently diluted with additional liquid or solid adjuvants to produce ultimate treating compositions. Good results are obtained when employing compositions containing from about 1 to about 20 pounds per acre of active material for pre-emergent application and from about 0.5 to about $4 \times 10^3$ parts per million by weight (p.p.m.) of active agent for antimicrobial applications.

In representative operations, the products of the invention when tested for antimicrobial activity using conventional agar dilution tests gave complete growth inhibition against the following organisms at the indicated concentrations in parts per million.

| Organism | Inhibitory Concentrations, ppm Compound* | | |
|---|---|---|---|
| | 1 | 2 | 3 |
| Staph aureus | 100 | 50 | 10 |
| Candida albicans | 50 | 50 | —[b] |
| Trichophyton mentagrophytis | 10 | 10 | 50 |
| Penicillium chrysogenosum | 50 | 50 | —[b] |
| Aspergillus niger | 50 | 50 | 50 |
| Bacillus subtilis | 100 | 50 | 50 |
| Candida pelliculosa | 50 | 50 | —[b] |
| E. Coli | 500 | —[c] | NT[a] |
| Psoteus mirabilis AV 21 | 500 | —[c] | NT[a] |
| Candida albicans NIH | 50 | 50 | —[b] |
| Aspergillus Fumigans Med Col VI | 50 | 50 | —[b] |
| Trichoderm sp. Madison P-42 | 100 | 50 | —[b] |
| Pullularia Pullulans | 50 | 50 | 100 |
| Salmonella typhosa | 500 | 100 | — |

[a]"NT" denotes not tested
[b]"—" denotes no control at 100 ppm
[c]"—" denotes no control at 500 ppm
*Compound 1 is pentachlorophenyl ester of (2-(1-oxopropoxy)ethyl)carbamic acid
Compound 2 is 2,4-dichloro-1-naphthyl ester of (2-(1-oxopropoxy)ethyl)carbamic acid
Compound 3 is 2-(1-methylpropyl)-4,6-dinitrophenyl ester of (2-(1-oxopropoxy)ethyl)carbamic acid When applied at a dosage rate of from about 0.5 to about $4 \times 10^3$ parts per million, each of the compounds of the present invention, the utility of which is not specifically exemplified above, has the ability to kill and control one or more of the hereinabove listed pests as well as other pests of the same class or classes.

The compounds of the present invention are also suitable for use in methods for the pre- and post-emergent control of weeds or other unwanted vegetation, particularly broadleaf plants.

EXAMPLE 4

In representative pre-emergence operations, seeds of various plant species are planted in seed beds, and while exposed, sprayed with compositions containing an active ingredient of the present invention. The treated seeds are then covered with a layer of soil and the test beds maintained under conditions conducive to growth for a period of 14 days. In representative general pre-emergence operations, Compound 1 (as set forth in Table 1) gave complete control of the growth of pigweed, crabgrass and yellow foxtail at an application rate of 10 lbs/acre. The 2-cyano-6-nitrophenyl ester of (2-(1-oxopropoxy)ethyl)carbamic acid gave 98% control of the growth of velvet leaf at an application rate of 10 lbs/acre. Compound 3, as set forth in Table 1, gave complete control of the growth of sugar beets and jimson weeds at an application rate of 2 lbs/acre and at 10 lbs/acre gave substantially complete (70-100%) control of the growth of cotton, pigweed, crabgrass, yellow foxtail, morning glory, wild oats and barnyard grass.

EXAMPLE 5

Representative compounds of the present invention were evaluated for post-emergence control of various plant species. In these evaluations, plots of plants grown to a height of about 4 inches were used. Aqueous spray compositions, each containing 4,000 ppm of active ingredient, were applied to separate plots. The application was made to the point of run-off and was carried out with conventional spraying equipment. Other plots were sprayed with similar compositions containing no toxicant to serve as controls. Thereafter, the plots were maintained under conditions conducive for plant growth. Two weeks after treatment, the plots were examined for plant growth and evaluated.

In representative general post-emergence operations, Compound 1, as set forth in Table 1, was found to give substantial to complete, i.e., from about 70 to about 100%, control of the growth of cotton, pigweed, barnyard grass, and velvet leaf. The 2-cyano-6-nitrophenyl ester of (2-(1-oxopropoxy)ethyl)carbamic acid gave complete control of the growth of velvet leaf, cotton and pigweed. Compound 3, as set forth in Table 1, gave substantial to complete control of the growth of crabgrass, yellow foxtail, morning glory, velvet leaf and barnyard grass.

In further embodiments, the compounds of the present invention or compositions containing the same, can be advantageously employed in combination with one or more additional pesticidal compounds. Such additional pesticidal compounds may be insecticides, nematocides, arthropodicides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use, or as an additament. The compounds in combination can generally be present in the ratio of from 1 to 100 parts of the compound of the present invention with from 100 to 1 parts of the additional compound(s).

STARTING MATERIALS

The phenol, naphthol and isocyanatoethyl compounds, described herein and employed as starting materials, are all known compounds.

I claim:

1. A compound of the formula

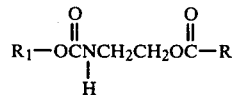

wherein

R represents 1-8C alkyl, phenyl or naphthyl, said phenyl and naphthyl groups being optionally substituted with one or more halo, nitro, cyano, 1-8C alkoxy, 1-8C alkyl or 1-8C alkylthio groups; and $R_1$ represents phenyl or naphthyl optionally substituted with one or more halo, nitro, 1–8C alkoxy, 1–8C alkyl, cyano, or 1–8C alkylthio groups.

2. The compound of claim 1 which is a 2,4,5-trichlorophenyl ester of [2-(acetyloxy)ethyl]carbamic acid corresponding to the formula

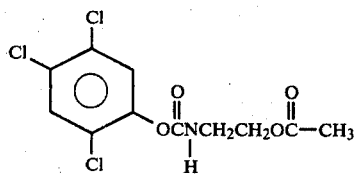

3. The compound of claim 1 which is a 2-(1-methylpropyl)-4,6-dinitrophenyl ester of [2-(1-oxopropoxy)ethyl]carbamic acid corresponding to the formula

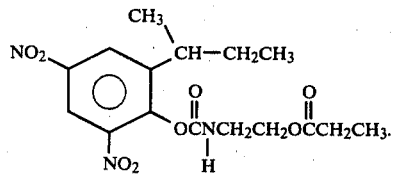

4. The compound of claim 1 which is a pentachlorophenyl ester of [2-(1-oxopropoxy)ethyl]carbamic acid corresponding to the formula

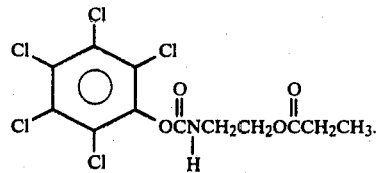

5. The compound of claim 1 which is a 2,4-dichloronaphthyl ester of [2-(1-oxopropoxy)ethyl]carbamic acid corresponding to the formula

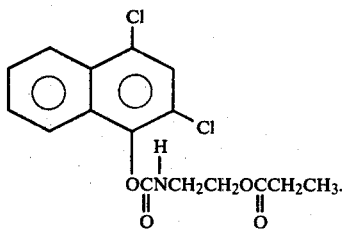

6. The compound of claim 1 which is a 2-cyano-6-nitrophenyl ester of [2-(1-oxopropoxy)ethyl]carbamic acid corresponding to the formula

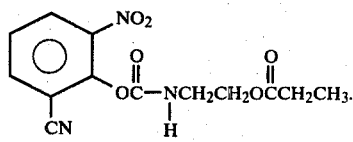

* * * * *